United States Patent [19]

Insell

[11] Patent Number: 4,855,051

[45] Date of Patent: Aug. 8, 1989

[54] MICROBIAL TREATMENT OF WASTEWATER TO REMOVE TERTIARY BUTYL ALCOHOL

[75] Inventor: James P. Insell, London, Canada

[73] Assignee: Polysar Limited, Sarnia, Canada

[21] Appl. No.: 48,613

[22] Filed: May 11, 1987

[51] Int. Cl.$^4$ ............................ C02F 3/00; C12R 1/06; C12R 1/07; C12R 1/38

[52] U.S. Cl. .................................... 210/601; 210/611; 435/247; 435/252.5; 435/253.3; 435/262; 435/830; 435/832; 435/874

[58] Field of Search ................ 210/601, 611; 435/245, 435/247, 250, 249, 253, 262, 830, 832, 874, 252.5, 253.3

[56] References Cited

U.S. PATENT DOCUMENTS

| | | | |
|---|---|---|---|
| 4,391,887 | 7/1983 | Baumgarten et al. | 435/245 X |
| 4,452,894 | 6/1984 | Olsen et al. | 435/875 X |
| 4,477,570 | 10/1984 | Colaruotolo et al. | 435/253 |
| 4,490,471 | 12/1984 | Ghisalba et al. | 435/247 X |
| 4,511,657 | 4/1985 | Colaruotolo et al. | 435/245 X |

Primary Examiner—David M. Naff
Attorney, Agent, or Firm—Stevens, Davis, Miller & Mosher

[57] ABSTRACT

The novel bacterial strains *Bacillus coagulans* ATCC 53595, *Arthrobacter globiformis* ATCC 53596 and *Pseudomonas stutzeri* ATCC 53602 are able to catabolize tertiary butyl alcohol and are therefore useful in treating wastewater to remove the compound prior to discharge.

4 Claims, No Drawings

MICROBIAL TREATMENT OF WASTEWATER TO REMOVE TERTIARY BUTYL ALCOHOL

FIELD OF THE INVENTION

This invention relates to novel microorganisms useful in degrading tertiary butyl alcohol.

BACKGROUND OF THE INVENTION

Tertiary butyl alcohol, hereafter referred to as TBA, is a four carbon aliphatic alcohol that due to its intrinsic quaternary structure is extremely resistant to biodegradation. Williams et al (1966) showed that the alcohol dehydrogenase of a species of Pseudomonas was ineffective with tertiary alcohols, yet functioned well with linear and secondary structured alcohols. This finding accounted for the inability of several investigators to degrade tertiary alcohols with activated sludges and microbial isolates (Hatfield, 1957; McKinney et al., 1955, Mohanrao et al, 1962). In the treatise on the bacterial genus Pseudomonas by Stanier et al, (1966), 267 stains of Pseudomonas were examined for their biochemical characteristics. None of the strains examined were reportedly able to metabolize tertiary alcohols.

Dias and Alexander (1971) examined the effect of chemical structure on the biodegradabilty of aliphatic acids and alcohols by microorganisms in sewage sludge. These workers found a relationship between substitution and the rate of degradation. Alpha substituted alcohols showed the greatest resistance to biodegradation. Beta substitution was less refractile than alpha but greater than omega substitution. While the usual group substitution was a halogen, the study did succeed in showing that chemical structure was related to biodegradation. It is generally understood, however, that tertiary structured compounds are extremely resistant to biodegradation since the primary carbon is completely methylated.

There remains, therefore, a need to identify bacteria which are capable of degrading TBA and to make these bacteria available for use in wastewater treatment plants required to handle significant concentrations of the compound.

SUMMARY OF THE INVENTION

It is an object of the present invention to provide novel bacteria capable of degrading tertiary butyl alcohol.

It is a further object of the present invention to provide a process which utilizes such novel bacteria to degrade tertiary butyl alcohol, particularly as applied to wastewater treatment systems.

It is a further object of the present invention to provide a process by which tertiary butyl alcohol may be removed from wastewater within a period of time practical to modern wastewater treatment systems.

One aspect of the present invention comprises three novel bacterial which are capable of degrading TBA either individually or collectively. These novel bacteria are herein designated *Bacillus coagulans* ATCC 53595; *Arthrobacter globiformis* ATCC 53956 and *Pseudomonas stutzeri* ATCC 53602. Clones and sub-clones thereof are comprised by the invention, as well.

Specimens of the bacteria have been deposited in the American Type Culture Collection (12301 Parklawn Drive, Rockville, Md, U.S.A.) and have been assigned the following accession numbers:

| Bacteria | Accession Number |
| --- | --- |
| 1. *Bacillus coagulans* | ATCC 53595 |
| 2. *Arthrobacter globiformis* | ATCC 53596 |
| 3. *Pseudomonas stutzeri* | ATCC 53602 |

Each novel bacterium is capable not only of degrading TBA but also of degrading it to an extent and over a period of time which is desirable in view of the process flow requirements of modern wastewater treatment facilities.

Accordingly, another aspect of the present invention resides in a process of degrading TBA which comprises maintaining a composition containing TBA in the presence of any one or a combination of the novel bacteria of the invention. Since phenol is also degraded by these bacteria, degradation of phenol constitutes a further, significant aspect of the invention.

The process aspect of the invention is most applicable to removing TBA from wastewater. Discharge of effluent containing high levels of total organic carbon (TOC) burdens the environment and particularly lakes and streams with the task of oxidizing the organic compounds. This process commits portions of useable oxygen to the detriment of organisms such as fish and flora, resulting in a lowering of life form quality. In some petrochemical processes, effluent streams can be comprised largely of TBA. In those instances and others, therefore, the novel bacteria of the present invention are used advantageously to lower the TOC of the effluent by removing TBA.

DETAILED DESCRIPTION OF THE PREFERRED EMBODIMENTS

The basis for the species designations used herein appears in Example 3. In general, each strain conforms to the criteria established as characteristic of the designated species. Notably, each strain has the further distinguishing characteristic of degrading TBA.

Each of the novel strains is currently maintained in viable form in the culture collection of The American Type Culture Collection in Rockville, Md. Access to these cultures will be available during pendency of the patent application to one determined by the Commissioner to be entitled thereto under 37 C.F.R. 1.14. All restrictions on availability of the cultures so deposited will be irrevocably removed upon the granting of the patent.

These novel bacterial strains were isolated from a broth of soil, silt, water and effluent taken from various sources in and around Sarnia, Ontario, Canada which was incubated using standard enrichment techniques. The broth was repeatedly subcultured and the resultant bacterial strains were isolated and tested in pure culture and mixed culture for catabolism of TBA.

Those strains which, after enrichment, exhibited growth in broth containing 0.1% TBA were subsequently tested for TBA degrading activity. Of the numerous strains contained in the original and continuously supplemented broth, only the novel strains identified herein were found to have the capacity to degrade TBA to a desirable extent within a suitable time period. Since these characteristics were not noted prior to enrichment, it is presumed that the trait was developed during culturing and sub-culturing and that, therefore, the novel bacteria are variant strains of the respective wild-type species.

The bacteria herein each show the capacity to degrade an appreciable amount of TBA within a 72 hour period. This time period is significant when modern wastewater treatment facilities are considered. The rate at which the wastewater is moved through the system and is ultimately discharged is a controlling factor in terms of efficiency of the unit. Obviously, it would be economically desirable to reduce the resident time of the wastewater in the bioreactor to increase the volume of wastewater treated by the unit. However, it is equally obvious that short resident times may prevent proper degradation of pollutants by activated sludge.

Under the conditions tested herein and exemplified in Examples 1 and 2 the bacteria are each capable of degrading at least 70% of available TBA within 72 hours of initial contact. Where shorter resident times are practical, TBA may be removed to an extent which still is significant e.g. 25-70%. Specifically, the bacteria have been shown to degrade TBA contained in a 1,000 ppm TBA composition to the following extents, under the conditions tested: B. coagulans ATCC 53595-70% degradation of TBA; P. stutzeri ATCC 53602-85% degradation; A globiformis ATCC 53596-98%.

In the aspect of the invention relating to wastewater treatment, the selected bacterium or bacteria is seeded in an activated sludge aeration tank into which TBA-containing effluent is to be discharged. The size of the bacterial inoculum seeded in the sludge will depend on several factors, as is usual, including the projected resident time of the wastewater containing TBA, the TBA concentration, the availability of other carbon sources and the interaction of the microbial flora.

On the basis of tests conducted to date, it appears that each of B. coagulans ATCC 53595, A. globiformis ATCC 53596 and P. stutzeri ATCC 53602 are each able to colonize the activated sludge without interference in a competitive sense by other indigenous bacteria and microflora. The viability of the bacteria in any selected sludge is easily confirmed using conventional experimental procedures, if necessary.

In addition, it is evident that despite the availability of other carbon sources such as phenols and glucose which is generally accepted as being preferred substrates by microbes, TBA is degraded by the bacteria. When the bacteria are presented with both TBA and phenol, there is a notable preference for the phenol, however, making these bacteria suitable also for degradation of phenol. Nevertheless, once a majority of the phenol concentration has been consumed, the bacteria will continue utilization of TBA as carbon source and degrade it efficiently. It may be postulated that the phenolic metabolism pathway and the TBA metabolism pathway are coupled, given these observations. The phenolic degradation using the bacteria of the present invention constitutes a further aspect of the present invention.

The bacteria each appear to tolerate a relatively wide range of TBA concentrations, from as low as about 10 ppm to about 2,000 ppm. It is unlikely that the lower range value will be encountered in wastewater treatment facilities since the TBA will be concentrated in the bioreactor. A more practical range therefore is from 500 ppm-2,000 ppm. This is not to suggest that higher concentrations cannot be tolerated by the organisms. However, higher bioreactor concentrations suggest improper primary control of process effluent and may be corrected prior to collection in the reactor. Should reactor concentrations exceed suitable levels, the bioreactor composition is preferably diluted.

Given these observations, it will be readily appreciated that B. coagulans ATCC 53595, A. globiformis ATCC 53596 and P. stutzeri ATCC 53602 are ideally suited for application in a wastewater treatment plant of industrial proportion. The bacteria are able to tolerate TBA concentrations in a range which it can normally be expected to encounter in industrial treatments e.g. 10-2,000 ppm. Further, the bacteria are compatible with typical sludge microflora and should not therefore disrupt that ecological niche. In addition and importantly, the bacteria are each capable of degrading TBA to a desirable extent e.g. at least 25% and up to almost 100%, within periods of time suited to acceptable resident times of the wastewater in the bioreactor e.g. 72 hours.

The required population contained in the bioreactor inoculum will depend on several factors which will vary on a plant by plant basis, including resident time, anticipated TBA concentration, reactor size etc. The criteria will be apparent to those skilled in the art given the goal of reducing TBA levels to those which are acceptable environmentally.

Aspects of the present invention are described hereinafter by way of example only with reference to the accompanying drawing in which FIG. 1 represents graphically the degradation of phenol and TBA from a wastewater sample as analyzed by gas chromatography and described in Example 2.

EXAMPLE 1

ISOLATION OF BACTERIA

A qualitative approach was taken in order to develop bacteria having TBA degradation activity. Sludge, silt, water and soil samples were taken from the Sarnia Township creek, the Sarnia, London and Corunna (all of Ontario, Canada) sewage treatment plants as well as the effluent streams of the Polysar plant in Sarnia. The sludge samples were activated sludges from the various municipal treatment facilities. The soil and silt samples were taken from the side and bed of the township creek approximately ten feet upstream of the Scott Road bridge, located in Sarnia.

Soil samples were suspended in an aqueous solution of sodium chloride (5.0 gm of soil in 50 ml of 0.9 weight per cent NaCl solution) and agitated for from 30 seconds to 1 minute. The soil suspension (0.1 ml) was added to 50 ml of minimal salts with varying concentrations of TBA. Effluent samples (50 ml) were supplemented with minimal salts and the pH adjusted to 6.8. All cultures obtained using these procedures were incubated as 32° C. and aerated at approximately 150 cubic feet per minute on a reciprocating shaker.

Each sample was repeatedly subcultured over an extended period e.g. 4 months-2 years, and the resultant variant bacterial strains were isolated and tested in pure culture and mixed culture for catabolic activity of TBA. Taxonomic characterization was not conducted until after TBA-catabolic efficacy was demonstrated.

EXAMPLE 2

TBA CATABOLISM STUDY

A series of experiments were conducted to quantitatively determine the ability of cultures of B. coagulens ATCC 53595, A. globiformis ATCC 53596 and P. stutzeri ATCC 53602 to degrade TBA in a wastewater containing TBA and phenols.

Minimal salts were prepared according to the following composition:

0.1% K$_2$HPO$_4$
0.1% KH$_2$PO$_4$
0.1% NH$_4$NO$_3$
0.025% MgSO$_4$.6H$_2$O
0.001% FeCl$_3$

Wastewater containing approximately 1000 ppm TBA plus phenols and other waste organics was adjusted to pH 7.0 and minimal salts and the bacterial cultures were added. The mixtures were cultured for 72 hours at 29° C..

TBA concentrations were determined according to the following procedure:

1. Samples of the mixture were centrifuged at 13,400g in a microfuge for 5 minutes at 20° C.
2. 1 to 5 ul of the supernatant were injected into a gas chromatograph equipped with an integrator.

The detector temperature was 170° C. with a column temperature of 160° C..

Table 1 illustrates the results of the experiments.

TABLE 1

| Experiment | Bacterial Culture | % TBA Degradation |
| --- | --- | --- |
| 1 | B. coagulans ATCC 53595 | 75 |
| 2 | P. stutzeri ATCC 53602 | 85 |
| 3 | A. globiformis ATCC 53596 | 98 |

EXAMPLE 3

CLASSIFICATION OF BACTERIA

The bacteria were subjected to biochemical testing and identified using the standard methods of classification as outlined in Bergey's Manual for Determinative Bacteriology, Manual of Methods for General Bacteriology and Biochemical Tests for Identification of Medical Bacteria. The bacterial cultures were isolated and stained with the Gram stain. Following morphological examination, the colonies grown on TBA were characterized as to shape, size, configuration, opaqueness and texture.

The results of biochemical testing appear below in Table 2.

TABLE 2

| TEST | Bacillus coagulans ATCC 53595 | Arthrobacter globiformis ATCC 53596 | Pseudomonas stutzeri ATCC 53602 |
| --- | --- | --- | --- |
| Gram test | positive | positive | negative |
| H$_2$S production | negative | negative | negative |
| Citrate | negative | negative | positive |
| Litmus milk | negative | positive | negative |
| Motility | motile | non-motile | motile |
| Starch hydrolysis | positive | positive | positive |
| Catalase | positive | positive | positive |
| Lactose ferm. | negative | positive | negative |
| Glucose ferm. | negative | negative | negative |
| Gelatine liquefaction | positive | positive | negative |
| Desoxycholate agar | no growth | no growth | growth |
| Violet red bile agar | no growth | no growth | no growth |
| 7.5% CaCl Nutrient agar | no growth | no growth | no growth |
| Hydrolysis of ONPG | negative | negative | negative |
| Arginine dihydrolase | positive | negative | negative |
| Lysine decarboxylase | negative | negative | negative |
| Ornithine decarboxylase | negative | negative | negative |
| Urease | negative | negative | negative |
| Mannitol | negative | negative | negative |
| Inositol | negative | negative | negative |
| Soritol | negative | negative | negative |
| Rhamnose | negative | negative | negative |
| Sucrose | negative | negative | negative |
| Melibiose | negative | negative | negative |
| Amygdalin | positive | negative | negative |
| Arabinose | negative | negative | negative |
| Tryptophane deaminase | negative | negative | negative |
| Indole production | negative | negative | negative |
| Acetoin production | negative | negative | negative |
| Nitrate reduction | negative | negative | negative |
| Oxidase | negative | positive | positive |

In addition to the above, it was determined that *Bacillus coagulans* ATCC 53595 is a gram positive spore-forming bacillus, *Arthrobacter globiformis* ATCC 53596 is a gram positive filamentous rod and *Pseudomonas stutzeri* ATCC 53602 is a gram negative short rod.

What is claimed is:

1. A process for treating wastewater containing tertiary butyl alcohol so as to reduce the tertiary butyl alcohol content thereof which comprises growing in the presence of said wastewater a population of a biologically pure culture of a bacterium selected from the group consisting of *Bacillus coagulans* ATCC 53595, Arthrobacter *globi formis* ATCC 53596 and *Pseudomonas stutzeri* ATCC 53602.

2. The process according to claim 1 wherein said bacterium is seeded into activated sludge prior to growing in the presence of said wastewater.

3. The process according to claim 2 wherein the concentration of tertiary butyl alcohol in the wastewater is from 10 to 2,000 ppm.

4. The process according to claim 2 wherein said bacterium is grown in the presence of said wastewater for a period of time not exceeding 72 hours.

* * * * *